United States Patent
Lang et al.

(10) Patent No.: US 7,109,387 B2
(45) Date of Patent: Sep. 19, 2006

(54) PRODUCTION OF α-CHLOROISOPROPYL-SUBSTITUTED AROMATICS

(75) Inventors: Gabriele Lang, Mannheim (DE); Stephan Hueffer, Ludwigshafen (DE); Arno Lange, Bad Duerkheim (DE); Hans Peter Rath, Gruenstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/504,160

(22) PCT Filed: Feb. 24, 2003

(86) PCT No.: PCT/EP03/01877

§ 371 (c)(1),
(2), (4) Date: Aug. 23, 2004

(87) PCT Pub. No.: WO03/070674

PCT Pub. Date: Aug. 28, 2003

(65) Prior Publication Data

US 2005/0171392 A1    Aug. 4, 2005

(30) Foreign Application Priority Data

Feb. 25, 2002 (DE) .............................. 102 07 963

(51) Int. Cl.
*C07C 22/00* (2006.01)
(52) U.S. Cl. .................................................. 570/191
(58) Field of Classification Search .................... 570/1, 570/246, 247, 248, 250
See application file for complete search history.

(56) References Cited

U.S. PATENT DOCUMENTS

| | | | |
|---|---|---|---|
| 3,024,291 A | 3/1962 | Olah et al. | |
| 4,241,222 A | 12/1980 | MacLeay | |
| 4,767,885 A * | 8/1988 | Kennedy | 570/185 |
| 5,300,717 A | 4/1994 | Roehrscheid | |

FOREIGN PATENT DOCUMENTS

| | | |
|---|---|---|
| EP | 713 883 | 5/1996 |
| SU | 1 286 586 | 1/1987 |

OTHER PUBLICATIONS

Joseph P. Kennedy, et al., "New telechelic polymers and sequential copolymers by polyfunctional initiator-transfer agents (inifers)10. three-arm star telechelic polyisobutylenes carrying chlorine olefin or primary alcohol endgroups", Polymer Bulletin, vol. 4, pp. 67-74 1981.

M. Schappacher, et al., "Activated α-chloro ether and α-bromo ether end groups as propagating species for the living cationic polymerization of vinyl ethers", MACROMOLECULES, vol. 24, No. 8, pp. 2140-2142 1991.

Oskar Nuyken, et al., "Polymers with indane units by cationic polymerization", Makromol. Chem., Macromol. Symp. 60, 57-63 1992.

* cited by examiner

*Primary Examiner*—Johann Richter
*Assistant Examiner*—Chukwuma Nwaonicha
(74) *Attorney, Agent, or Firm*—Oblon, Spivak, McClelland, Maier & Neustadt, P.C.

(57) ABSTRACT

α-Chloroisopropyl-substituted aromatics are obtained in high yield by treating isopropenyl-substituted aromatics with hydrogen chloride gas in the absence of a solvent. The α-chloroisopropyl-substituted aromatics serve as initiators for the cationic polymerization of isobutene.

10 Claims, No Drawings

PRODUCTION OF α-CHLOROISOPROPYL-SUBSTITUTED AROMATICS

The present invention relates to a process for preparing α-chloroisopropyl-substituted aromatics.

α-Chloroisopropyl-substituted aromatics, such as m- or p-dicumyl chloride or 1,3,5-tricumyl chloride, served as inifer molecules for preparing linear or star-shaped telechelic polyisobutenes. The reaction of the inifer with a Lewis acid results in a complex having 2 or 3 carbocationic or cationogenic centers which can add onto isobutene molecules. The carbocationic tert-butyl termini of the linear or star-shaped polyisobutenes obtained may be converted to olefinic or other functional groups, cf., for example, EP-A 0 713 883.

J. P. Kennedy, L. R. Ross, J. E. Lackey, O. Nuyken, Polym. Bull. 1981, 4, 67-74 describe the synthesis of 1,3,5-tris(α-chloroisopropylbenzene) by reacting 1,3,5-triisopropenylbenzene with hydrogen chloride in dichloromethane at 0° C. For the workup, the dichloromethane has to be distilled off.

On the other hand, O. Nuyken, G. Maier, D. Young, M. B. Leitner, Macromol. Chem., Macromol. Symp. 60, (1992) 57–63 disclose that 1,4-diisopropenylbenzene forms a polymer having 1,1,3-trimethylindane or α-methylstyrene repeating units under the influence of Lewis or Brönsted acids.

It is an object of the present invention to provide a process by which α-chloroisopropyl-substituted aromatics is obtained in high yield and with simple workups.

We have found that this object is achieved by a process for preparing α-chloroisopropyl-substituted aromatics of the formula I

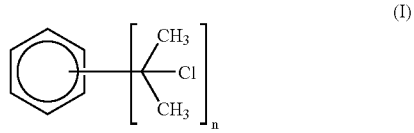

where n is an integer from 2 to 4 be treating isopropenyl-substituted aromatics of the formula II

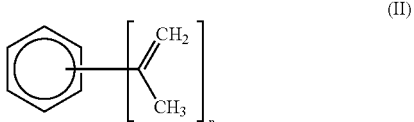

with hydrogen chloride in the absence of a solvent.

The process according to the invention allows α-chloroisopropyl-substituted aromatics to be obtained in virtually quantitative yields. This is surprising to a high degree, since those skilled in the art would have expected a reaction in the absence of a solvent to result in the occurrence of numerous undesired secondary reactions or the cationic polymerization of the isopropenyl-substituted aromatics (cf. O. Nuyken et al., loc. cit.). The success of the process according to the invention is believed to be based on the instability of carbocations, from which undesired secondary reactions or polymerizations can start, in the absence of a solvent, in particular of a polar solvent.

The process according to the invention can be carried out in a simple manner by passing hydrogen chloride gas through the isopropenyl-substituted aromatics or by reacting it therewith in a pressure vessel. This utilizes the fact that both the reactant and the product of the process according to the invention are liquid at reaction temperature and that the use of a solvent is unnecessary. The workup is generally limited to the removal of excess hydrogen chloride gas from the product, for example by stripping with inert gas such as nitrogen. Yield losses resulting from workup steps are avoided.

The process according to the invention is preferably effected at a temperature of from −10 to +50° C., in particular from 0 to 15° C., and a pressure from 1 to 10 bar. It may be carried out batchwise or continuously.

The reaction may optionally be accelerated by using Lewis or Brönsted acid catalysts. Useful catalysts include Lewis acids such as aluminum trichloride, aluminum tribromide, boron trifluoride, boron trifluoride alkoxide, boron trifluoride etherate, titanium tetrachloride, tin tetrachloride, ethylaluminum dichloride, iron trichloride, antimony pentachloride or antimony pentafluoride; Brönsted acids such as sulfuric acid, phosphoric acid, trifluoromethanesulfonic acid and the like. Organic protic acids may also be present in polymerically bound form, for example as ion exchanger resins.

In the formulae I and II, n is preferably 2 or 3. Preferred isopropenyl-substituted aromatics are 1,3,5-triisopropenylbenzene, 1,4-diisopropenylbenzene and 1,3-diisopropenylbenzene, and particular preference is given to the latter. Apart from the isopropenyl substituents, the benzene ring may bear further substituents which do not impair the reaction according to the invention, in particular $C_1$-$C_4$-alkyl radicals such as methyl, ethyl or t-butyl. Useful reactants for the process according to the invention also include mixtures of different isopropenyl-substituted aromatic.

The isopropenyl-substituted aromatics used as reactants are known and obtainable, for example, by dehydrating α-hydroxyl-substituted aromatics (cf. DE-A 1 618 449), Wittig reaction of acetylbenzenes (cf. J. P. Kennedy et al., Polym. Bull. 1981, 4, 67–74) or by dehydrogenating isopropylbenzenes (cf. JP-2001026558 and JP-2000327596).

The α-chloroisopropyl-substituted aromatics obtained by the process according to the invention can be used in a manner known per se for preparing homopolymers of isobutene or copolymers of isobutene with vinylaromatics by living cationic polymerization. On this subject, reference is made, for example, to EP-A 0 713 883, DE-A 199 37 562 or DE-A 100 61 715.

The invention is illustrated by the examples which follow.

EXAMPLE 1

A 1 l four-necked flask was initially charged with 500 g (3.16 mol) of 1,3-diisopropenylbenzene. 290 g (7.95 mol) of hydrogen chloride were passed in within 7.5 h with cooling to an internal temperature of 5° C. and at atmospheric pressure. Unconverted HCl was then removed by stripping with nitrogen. 715 g (98%) of 1,3-bis(α-chloroisopropyl)benzene remained as a colorless liquid; chlorine content 29.3%; $^1$H-NMR ($CD_2Cl_2$, 360 MHz): 2.00 (s, 12 H, methyl), 7.29–7.52 (m, 3 H, aromat. H), 7.82–7.83 (m, 1 H, aromat. H).

EXAMPLE 2

A 500 ml four-necked flask was initially charged with 200 g (1.26 mol) of 1,3-diisopropenylbenzene. 135 g (3.70 mol) of hydrogen chloride were passed in within 8 h with cooling to an internal temperature of 5° C. and at atmospheric pressure. Unconverted HCl was then removed under reduced pressure. 288 g (99%) of 1,3-bis(α-chloroisopropyl)benzene remained as a colorless liquid; chlorine content 28.6%; $^1$H-NMR (CD$_2$Cl$_2$, 360 MHz): 2.00 (s, 12 H, methyl), 7.29–7.52 (m, 3 H, aromat. H), 7.82–7.83 (m, 1 H, aromat. H).

COMPARATIVE EXAMPLE 3

A 2 l four-necked flask was initially charged with 200 g (1.26 mol) of 1,3-diisopropenylbenzene in 750 ml of CH$_2$Cl$_2$ and this was then admixed with about 1 ml of ethanol. 12.5 g (3.42 mol) of hydrogen chloride were passed in within 7 h with cooling to an internal temperature of 5° C. and at atmospheric pressure. The solvent and also unconverted HCl was then removed under reduced pressure. 264 g (90%) of 1,3-bis(α-chloroisopropyl)benzene remained as a colorless liquid; chlorine content 29.2%; $^1$H-NMR (CD$_2$Cl$_2$, 360 MHz): 2.00 (s, 12 H, methyl), 7.29-7.52 (m, 3 H, aromat. H), 7.82-7.83 (m, 1 H, aromat. H).

EXAMPLE 4

An autoclave was initially charged with 490 g (3.10 mol) of 1,3-diisopropenylbenzene. 200 g (5.6 mol) of HCl were metered in within 3 h in such a manner that the internal pressure was 5 bar and the internal temperature did not exceed 30° C. The remaining HCl was removed by stripping with nitrogen. 705 g (99%) of 1,3-bis(α-chloroisopropyl)benzene were obtained as a colorless liquid; chlorine content 30.6%; $^1$H-NMR (CD$_2$Cl$_2$, 360 MHz): 2.00 (s, 12 H, methyl), 7.29-7.52 (m, 3 H, aromat. H), 7,82-7,83 (m, 1 H, aromat. H).

EXAMPLE 5

A 40 l V4A steel stirred reactor was initially charged with 18.0 kg (114 mol) of 1,3-diisopropenylbenzene. 10.1 kg (277 mol) of hydrogen chloride were passed in within 8 h at an internal temperature of 5-10° C. (brine cooling) and an internal pressure of 1.1 bar. The remaining HCl was removed by stripping with nitrogen. 26 kg (99%) of 1,3-bis(α-chloroisopropyl)benzene were obtained as a colorless liquid; chlorine content 30.1%; $^1$H-NMR (CD$_2$Cl$_2$, 360 MHZ): 2.00 (s, 12 H, methyl), 7.29–7.52 (m, 3 H, aromat. H), 7.82-7.83 (m, 1 H, aromat. H).

We claim:
1. A process for preparing α-chloroisopropyl-substituted aromatics of the formula I

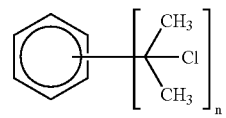

where n is an integer from 2 to 4
comprising treating at least one isopropenyl-substituted aromatic of the formula II

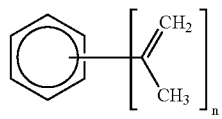

with hydrogen chloride in the absence of a solvent,
wherein the benzene ring of the isopropenyl-substituted aromatic of formula (II) may optionally bear one or more substituents which do not impair reaction of said aromatic of formula (II) and hydrogen chloride, whereby the benzene ring of the α-chloroisopropyl-substituted aromatics of the formula I will bear the same substituents.

2. A process as claimed in claim 1, wherein the treatment is effected at a temperature of from −10 to 50° C.

3. A process as claimed in claim 1, wherein the treatment is effected at a pressure of from 1 to 10 bar.

4. A process as claimed in claim 1, wherein said isopropyl isopropenyl-substituted aromatic of the formula II is 1,3-diisopropenylbenzene.

5. A process as claimed in claim 1, wherein the treatment is accelerated by the presence of a Lewis or Brönsted acid catalyst.

6. A process as claimed in claim 2, wherein the treatment is effected at a temperature of from 0 to 15°C.

7. A process as claimed in claim 1, wherein n is 2 or 3.

8. A process as claimed in claim 1, wherein the isopropenyl-substituted aromatic of formula (II) is at least one of 1,3,5-triisopropenylbenzene, 1,4-diisopropenylbenzene and 1,3-diisopropenylbenzene.

9. A process as claimed in claim 1, wherein the benzene ring of the isopropenyl-substitued aromatic of formula (II) bears said one or more substituents.

10. A process as claimed in claim 9, wherein the substituents are selected from the group consisting of $C_1$–$C_4$-alkyl radicals.

* * * * *